US00PP22623P2

(12) United States Plant Patent
Zerr

(10) Patent No.: US PP22,623 P2
(45) Date of Patent: Apr. 3, 2012

(54) POINSETTIA PLANT NAMED 'SYEP0791'

(50) Latin Name: *Euphorbia pulcherrima*
Varietal Denomination: SYEP0791

(75) Inventor: Katharina Zerr, Hillscheid (DE)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/932,455

(22) Filed: Feb. 25, 2011

(51) Int. Cl.
*A01H 5/00* (2006.01)

(52) U.S. Cl. ..... Plt./307

(58) Field of Classification Search ..... Plt./307
See application file for complete search history.

*Primary Examiner* — Kent L Bell
(74) *Attorney, Agent, or Firm* — S. Matthew Edwards

(57) ABSTRACT

A new Poinsettia plant named 'SYEP0791' particularly distinguished by its bright red bract color, ovate bract shape, medium sized, horizontally shaped inflorescences, dark green foliage, leaf without lobes, medium sized, v-shaped plant habit, and early flowering.

1 Drawing Sheet

Latin name of the genus and species of the plant claimed: *Euphorbia pulcherrima.*

Varietal denomination: 'SYEP0791'.

BACKGROUND OF THE NEW PLANT

The present invention comprises a new Poinsettia plant, botanically known as *Euphorbia pulcherrima*, and hereinafter referred to by the variety name 'SYEP0791'.

'SYEP0791' is a product of a planned breeding program. The new cultivar 'SYEP0791' has bright red colored, ovate bracts, dark green foliage, leaves nearly without any lobes, medium sized, v-shaped plant habit, and early flowering.

'SYEP0791' originated as a naturally occurring whole plant mutation of the parent variety 'Fismars' discovered by the inventor in November 2007 in a Poinsettia trial in Ahlem near Hannover, Germany. 'Fismars' has been disclosed in U.S. Plant Pat. No. 14,977. 'Fismars' has medium red bracts, dark-green foliage, and about mid season start of flowering.

As an earlier flowering line might be desirable, the mutated plant, 'SYEP0791', was taken to Hillscheid, Germany, for further examination and for evaluation of the stability of the new feature.

The first act of asexual reproduction of 'SYEP0791' was accomplished when shoot tips were cut and rooted in the spring of 2008. The resulting plants were grown out and in the end of July 2008 propagated and cultivated for the first trial in the fall and winter of 2008.

Horticultural examination of plants grown from cuttings of the plant initiated in the summer of 2008 in Hillscheid, Germany, and continuing thereafter on a larger scale, has demonstrated that the combination of characteristics as herein disclosed for 'SYEP0791' are firmly fixed and are retained through successive generations of asexual reproduction.

Plant Breeders' Rights for this cultivar were applied for in Canada on Mar. 8, 2010 (No. 10-6880), in the European Union on Nov. 4, 2010 (No. 2010/2356), and in Switzerland on Nov. 11, 2010 (No.10-2697). 'SYEP0791' has not been made publicly available more than one year prior to the filing of this application.

'SYEP0791' has not been observed under all possible environmental conditions. The phenotype may vary significantly with variations in environment such as temperature, light intensity and day length

DESCRIPTION OF DRAWING

The accompanying photographic drawings show typical flower and foliage characteristics of 'SYEP0791' with colors being as true as possible with an illustration of this type.

DETAILED BOTANICAL DESCRIPTION

Figure 1:
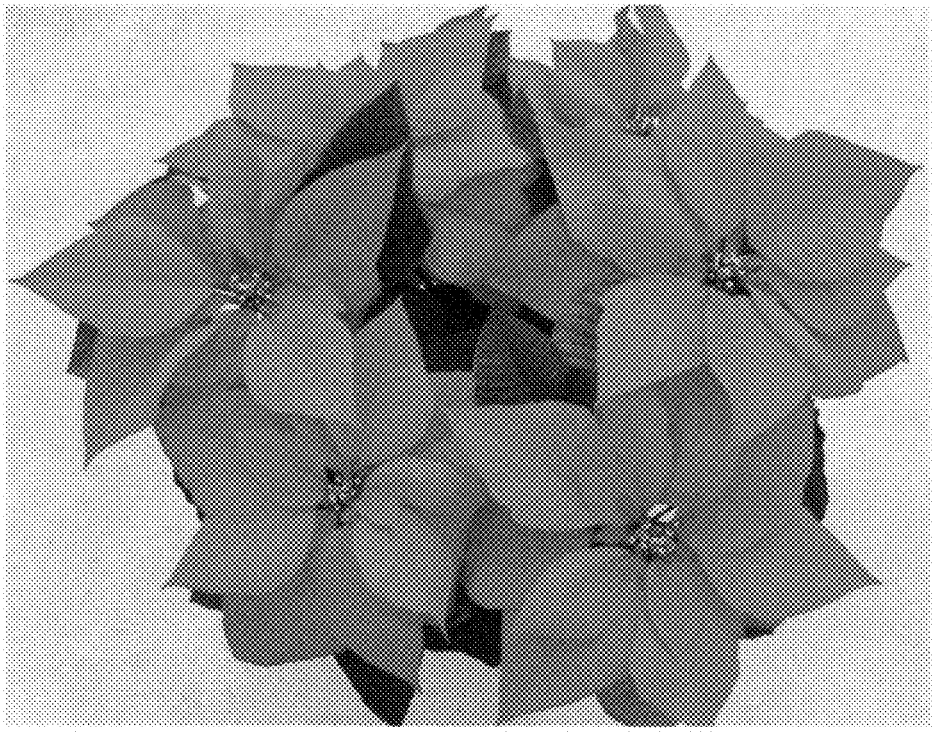
FIG. 1 is a top view of an 18 week old flowering plant taken in Monroeville, N.J.
Figure 2:
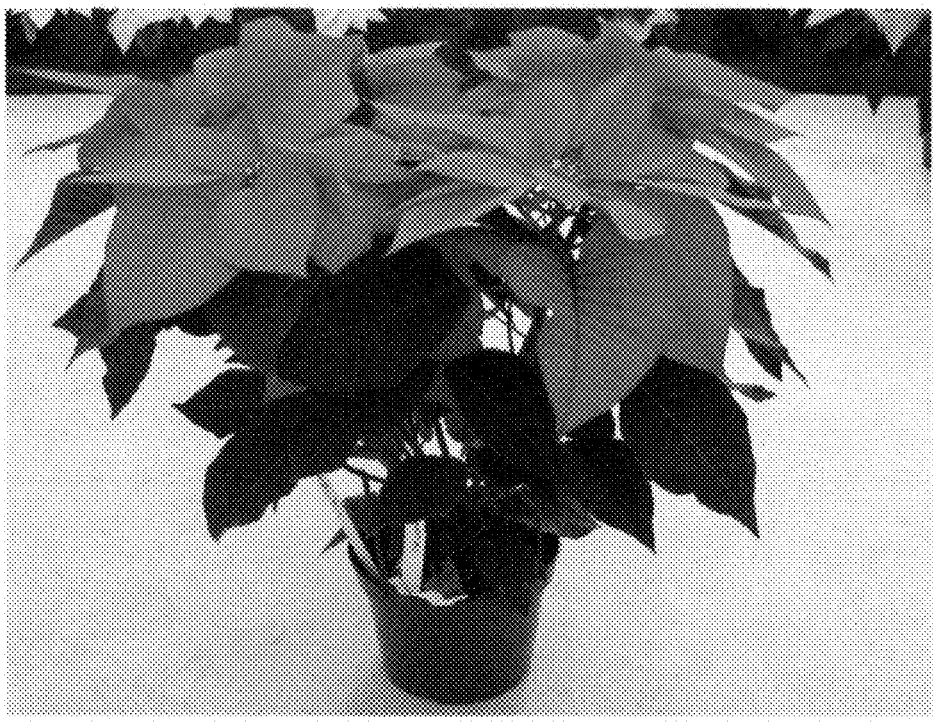
FIG. 2 shows a side view of the same plant.

The measurements were taken in Enkhuizen, Netherlands, on Dec. 16, 2010 on about 18 week old plants growing in a greenhouse. Cultivation of these plants had started on Aug. 10, 2010 when rooted cuttings were planted into 12 cm pots and pinched about 2 weeks later.

The plants were grown under natural day light in the fall (no black cloth was applied to initiate earlier flowering) and at the moderately warm temperature of 18°-20° C. for the bench heating.

Color Chart used: Royal Horticultural Society Colour Chart (R.H.S.) 2001

BRIEF SUMMARY OF INVENTION

The following observations, measurements, and comparisons describe plants grown on benches in a greenhouse in Hillscheid, Germany. The following traits have been repeatedly observed and are determined to be basic characteristics of the new variety. The combination of these characteristics distinguishes this Poinsettia plant as a new and distinct variety.

1. Bright red colored bracts with nearly no lobes
2. Medium to large sized inflorescences, with the bracts flat and overlapping
3. Dark green foliage, ovate leaves nearly without any lobes 4. About medium vigor, v-shaped habit with upright directed stems
5. Early flowering response
6. Good packing and transportation ability

DIFFERENCES BETWEEN THE NEW VARIETY 'SYEP0791' AND SIMILAR VARIETIES

'SYEP0791' has a similar bract color as the parent, the commercial variety 'Fismars', disclosed in U.S. Plant Pat. No. 14,977. 'SYEP0791' differs mainly by its earlier start of flowering, and by its slightly lower plant habit, yet larger inflorescences.

In contrast to 'Fismars 339' (U.S. Plant Pat. No. 21,054), 'SYEP0791' has a somewhat less deep red main flower bract color and earlier flowering.

In comparison to the commercial variety 'Freedom Red', patented under the designation '490', U.S. Plant Pat. No. 7,825, 'SYEP0791' has distinctly smaller bracts, edges of bracts and leaves with only very weak expression of lobes, and a narrower plant habit with more upright directed stems.

Plant:

*Form, growth and habit.*—Shrub, with the branches slanting upright at an angle of over 45 degrees, well-branched, about medium sized.

*Plant height (without pot).*—24-27 cm, average 25.7 cm.

*Plant width.*—39-45, average 41.3 cm.

*Number of branches.*—8-11, 9 on average.

*Number of inflorescences.*—7.5-8.5.

Root:

*Number of days to produce a rooted cutting/liner/young plant.*—24-25 days at a temperature of 22 to 24 degrees centigrade.

*Form.*—Self-branching, somewhat fleshy.

*Color.*—Near RHS N155B.

Stem:

*Color of stem.*—Mainly RHS 144B, mid portion overlain with anthocyanin color, approximately RHS 181C.

*Length of stem.*—Variable from 16-21 cm.

*Diameter at medium portion.*—0.5-0.6 cm.

*Length of internodes.*—From 2-4 cm.

*Texture.*—Smooth, glabrous.

Foliage:

*Arrangement.*—Alternate, single leaves.

*Quantity.*—6-8 leaves per branch.

*Aspect.*—Most petioles are horizontally directed, while the leaf blades show downwards.

*Immature leaf, color of upper surface.*—RHS 137D.

*Immature leaf, color of lower surface.*—RHS 137D or 138A.

*Mature leaf, color of upper surface.*—Near RHS 139A.

*Mature leaf, color of lower surface.*—RHS 138A.

*Leaf length.*—10.5-12.5; 11.8 cm on average.

*Leaf width.*—7.5-9.5; 8.6 cm on average.

*Shape.*—Ovate, without or with very weak lobes.

*Base shape.*—Obtuse.

*Apex shape.*—Acuminate.

*Margin.*—Entire.

*Venation.*—In a pinnate pattern, visible on the underside mainly.

*Color of veins, upper surface.*—Approximately RHS 182A at base, upper portion indistinct.

*Color of veins, lower surface.*—RHS 182C near base; green, RHS 138C near tip.

*Venation pattern.*—Pinnate.

*Texture of leaf blade.*—Both surfaces flat, smooth, apart from the protruding veins on the underside; glabrous on the upper side, very short, fine hair on the underside.

*Petiole color, upper surface.*—RHS 183B.

*Petiole color, lower surface.*—RHS 183C.

*Petiole length.*—From 4.5-7 cm.

*Diameter of petiole.*—0.3 cm.

*Texture of petiole.*—Upper and lower sides are smooth, glabrous.

Inflorescence:

*Type.*—Terminal cyme with surrounding whorl of colored flower bracts.

*Flowering, botanically (opening of the stamina, shedding of pollen).*—Late November.

*Flowering period, commercially (sufficiently colored bracts).*—From mid November.

*Flowering response time.*—About 8 weeks from equinox.

*Duration of flowering.*—Depends from light and environment, at least 4-8 weeks of 'shelf' life.

*Fragrance.*—Absent.

*Shape of inflorescence.*—Rosette-like arrangement, bracts mostly flat, overlapping and horizontally borne.

*Diameter of inflorescence.*—23-25 cm, average 24.3 cm.

*Inflorescence, vertical diameter.*—3-5 cm.

*Number of completely colored bracts per inflorescence (sized over 2 cm).*—12-14.

*Single bract, shape.*—Ovate, only occasionally with weak lobes.

*Bract, apex.*—Acuminate.

*Bract, base.*—Obtuse to rounded.

*Margin.*—Entire.

*Single bract, length of blade.*—12-14 cm, average 12.8 cm, younger bracts diminishing in size.

*Single bract, width of blade.*—7.5-11 cm, average 8.8 cm.

*Bract color, upper side.*—Between RHS 46B and 46C.

*Bract color, lower side.*—RHS 45D.

*Venation pattern.*—Pinnate.

*Vein color, upper surface.*—From RHS 53A at the base to RHS 53B near the tip.

*Vein color, lower surface.*—Green RHS 138D, or pink RHS 51C.

*Bract petiole length.*—About 1.5-2.5 cm, shorter for the younger bracts.

*Bract petiole diameter.*—2.5 mm.

*Petiole color, upper surface.*—RHS 145A (pale green) for the lowest bracts, RHS53A (purple-red) for the other ones.

*Petiole color, lower surface.*—RHS 145A for the lowest bract; near RHS 53D for the other ones.

*Texture of bract.*—Both surfaces are smooth and glabrous.

Cyme (true inflorescence):

*Cyme, diameter.*—1.5-2.5 cm.

*Number of cyathia.*—0 to 5 were observed.

*Cyathium, shape.*—Ovate.

*Cyathium, diameter.*—0.5 cm.

*Cyathium, length.*—0.7 cm.

*Color*.—Main color ranging from RHS 143A to 143B, at top RHS 46B.

*Peduncle length*.—2-3 mm.

*Peduncle color*.—RHS 143B.

*Nectar cups*.—Usually one per cyathium.

*Nectur cup, width*.—Mostly 5-6 mm.

*Nectar cup, color*.—Yellow, RHS 12A, no reddish coloring at the margin.

Reproductive organs:

*Stamen* (*actually reduced male florets*).—Usually in a small bunch of 15-20 at the top of the cyathium.

*Shape*.—Strap-like.

*Filament length*.—2-3 mm.

*Filament color*.—RHS 46B.

*Anther color*.—Yellow, RHS 11A.

*Anther diameter*.—1 mm.

*Pollen quantity*.—Moderate (normal quantity).

*Pollen color*.—RHS 12A.

*Pistils* (*actually female flowers*).—Have not been observed (may occur sparse in mid winter, occurrence depends much on light intensity).

*Fertility/seed set*.—No seed set observed.

Disease/pest resistance: Disease resistance or susceptibility has not been observed on this hybrid.

What is claimed is:

1. A new and distinct variety of Poinsettia plant named 'SYEP0791', substantially as illustrated and described herein.

* * * * *